(12) United States Patent
Ahnblad

(10) Patent No.: US 9,962,283 B2
(45) Date of Patent: May 8, 2018

(54) AID FOR SUPPORTING OF JAW ANGLE USED AGAINST SNORING AND SLEEP APNEA

(75) Inventor: Peter Ahnblad, Stockholm (SE)

(73) Assignee: ENTpro AB, Stockholm (SE)

( * ) Notice: Subject to any disclaimer, the term of this patent is extended or adjusted under 35 U.S.C. 154(b) by 381 days.

(21) Appl. No.: 14/006,699

(22) PCT Filed: Mar. 21, 2012

(86) PCT No.: PCT/SE2012/050309
§ 371 (c)(1),
(2), (4) Date: Oct. 11, 2013

(87) PCT Pub. No.: WO2012/128710
PCT Pub. Date: Sep. 27, 2012

(65) Prior Publication Data
US 2014/0048078 A1 Feb. 20, 2014

(30) Foreign Application Priority Data
Mar. 23, 2011 (SE) ...................................... 1100215

(51) Int. Cl.
*A61F 5/56* (2006.01)
*A61F 13/12* (2006.01)

(52) U.S. Cl.
CPC .............. *A61F 5/56* (2013.01); *A61F 13/122* (2013.01)

(58) Field of Classification Search
CPC .... A61F 5/56; A61F 13/02; A61F 5/37; A61F 5/3707; A61F 5/0003; A61F 5/0006;
(Continued)

(56) References Cited

U.S. PATENT DOCUMENTS

| 765,361 | A | * | 7/1904 | Hargrave | ............... A45D 44/22 132/333 |
| 2,649,857 | A | * | 8/1953 | O'Loughlin | ........... A45D 44/22 606/204.35 |

(Continued)

FOREIGN PATENT DOCUMENTS

| CA | 2236503 A1 | 5/1998 |
| CA | 2336604 A1 | 1/2000 |

(Continued)

OTHER PUBLICATIONS

International Search Report from corresponding International Application No. PCT/SE2012/050309, dated Jun. 25, 2012.
(Continued)

*Primary Examiner* — Victoria J Hicks
(74) *Attorney, Agent, or Firm* — Renner, Otto, Boisselle & Sklar, LLP; Grant Steyer

(57) ABSTRACT

An aid against snoring with a slingshot-shaped outer splint which support the jaw angle and fixates the lower jaw to the cheek and upper jaw. The splint is pressure relieving, pressure distributing, bendable and therefore individually adjustable and adheres to the support (skin) (FIG. 1) from the jaw angle to cheek and upper jaw (and alternatively up over the bridge of the nose) (FIG. 4 and FIG. 5) and in that way prevent the lower jaw from falling backwards-downwards and obstruct the air way in the throat during sleep.

4 Claims, 3 Drawing Sheets

(58) Field of Classification Search
CPC .. A61F 5/0009; A61F 5/00; A61F 5/01; A61F 5/05891; A61F 5/05883; A61F 13/122; A61F 13/12; A61F 13/124; A61F 13/128; Y10S 602/902; A61M 13/0694; A61M 16/0833; A42B 3/08; A63B 2244/108; A45D 44/22; A45D 44/00
USPC .......................... 132/333; 428/343; 128/848; 606/204.55; 433/140
See application file for complete search history.

(56) References Cited

U.S. PATENT DOCUMENTS

| | | | |
|---|---|---|---|
| 4,118,813 A | 10/1978 | Armstrong | |
| 4,366,815 A | 1/1983 | Broomes | |
| 4,748,702 A | 6/1988 | Sandler | |
| 4,817,636 A | 4/1989 | Woods | |
| 5,289,829 A | 3/1994 | Roehrig | |
| 5,640,974 A * | 6/1997 | Miller | A61F 5/08 128/845 |
| 5,868,769 A * | 2/1999 | Rosenblood et al. | 606/161 |
| D410,089 S * | 5/1999 | Schiavoni | D24/191 |
| D420,742 S * | 2/2000 | Noble | D24/146 |
| 6,109,265 A | 8/2000 | Frantz et al. | |
| 6,279,577 B1 * | 8/2001 | Savaiano | 128/848 |
| 6,668,834 B1 | 12/2003 | Zikria | |
| 6,918,394 B2 | 7/2005 | Matsuda et al. | |
| 7,331,349 B2 | 2/2008 | Brady et al. | |
| 7,456,332 B2 | 11/2008 | Beaudry | |
| 2003/0056785 A1 * | 3/2003 | Narihiko | A61F 5/56 128/201.26 |
| 2006/0058821 A1 * | 3/2006 | Jansheski | A61B 17/244 606/161 |
| 2006/0142445 A1 * | 6/2006 | Soerens | A61L 15/585 524/236 |
| 2007/0256694 A1 | 11/2007 | Kussick | |
| 2008/0115791 A1 | 5/2008 | Heine | |

FOREIGN PATENT DOCUMENTS

| | | |
|---|---|---|
| CN | 101422635 A | 5/2009 |
| DE | 202004012390 U1 | 9/2004 |
| DE | 202004012829 U1 | 12/2004 |
| GB | 190709828 A | 3/1908 |
| GB | 191323245 A | 7/1914 |
| GB | 191209390 A | 7/1918 |
| GB | 2264868 A | 9/1993 |
| JP | 11-76286 A | 3/1999 |
| JP | 2006-507025 | 4/2003 |
| JP | 2003093423 A | 4/2003 |
| JP | 2006175110 A | 7/2006 |
| WO | 02066111 A1 | 8/2002 |
| WO | 03/090791 A2 | 11/2003 |

OTHER PUBLICATIONS

Office Action for corresponding Japanese Patent Application No. 2014-501040 dated Dec. 17, 2015.

* cited by examiner

AID FOR SUPPORTING OF JAW ANGLE USED AGAINST SNORING AND SLEEP APNEA

TECHNICAL FIELD

The present invention relates to a supporting splint adapted for the jaw angle with fixation against cheek and upper jaw as an aid against snoring.

BACKGROUND ART AND TECHNICAL POINT OF VIEW

Snoring is a large global problem both for the person snoring but also for the partner. Approximately every third grown up snores regularly. The number of people snoring is estimated to increase in the future when the average length of life increases and elderly people generally snores more due to general weakening of the tissue and that people generally gains weight which creates a more narrow throat. On top of that problems with snoring are more and more brought to the fore in society.

During breathing variations in air pressure are arisen from nose to throat and to air pipes. The nose and the air pipes are normally stiff enough to handle the variations in pressure without collapsing. However, the throat is more soft and elastic but can normally also handle the variations in pressure because the muscles involuntarily stiffen the throat during inhalation. During sleep the muscles in the throat relaxes and the space available for the inhaled air decreases. This means that a physiological event crucial for snoring occurs, that is that the lower jaw and the chin together with the thong relaxes and falls backwards-downwards which substantially decreases the space in the throat. During inhalation the walls of the throat can be sucked together and bulge inwards. The particular snoring sound arises due to this sucking effect, a so called Bernoulli-effect, which creates a vibration in especially the soft palate and the rear throat wall. In longer term, this enlarges the tissue in the throat and creates a sensory disorder with a decreased sensitivity in the mucous membrane which even further increases the snoring sounds and snoring.

At least 10% of the snorers have on top of the snoring also respiratory interruptions during their sleep which gives a fragmentized sleep and a disrupted sleep pattern. The airways are temporarily blocked and the interruption of breathing creates an awakening reaction which makes the person gasp for breath. However, it is not certain that this is remembered when they wake up instead it is felt like a bad night's sleep. An interruption of breathing lasting for 10 seconds or more is called an apnea. Repeated sleep apnea during a longer time gives a lower level of oxygen in the blood and a substantial increased risk of cardiovascular decreases for example a high blood pressure, cardiac infarction or stroke and an increased risk for accidents in traffic and at work. The sleepiness during day can be so severe that the person can fall asleep during driving, when eating or during a conversation. Other symptoms can be irritation over small matters, aggressiveness, lack of ability to concentrate, depression or impotence.

As a first step of treatment and self-care of snoring it is recommended so called conservatory advises like for example losing weight, avoidance of alcohol, stop smoking and avoiding sleeping pills and similar muscle relaxing drugs and to avoid sleeping on the back, so called position training.

Often this is not enough or is not easily made and then there are additional treatments to be made which all involve a large step away from conservatory treatment such as palate and throat surgery or so called CPAP (Continuous Positive Airway Pressure); overpressure breathing with a face mask and an electric air pump, roughly explained as a mini respirator. The first mentioned treatment involves a relatively costly operation with a risk for complications due to the narcosis or local anesthetic, risk for infections and pain and period of convalescence. The last mentioned treatment imply a substantial stigmatization and also a high cost since the patient every night need to be attached to a buzzing machine with uncomfortable tubes and face mask.

Since the snoring problem is well known and wide spread globally, several techniques exist aimed at trying to maintain the space in the throat, beside the above mentioned and quite drastic measures involving operation or CPAP. These techniques are described below.

KNOWN AND DESCRIBED TECHNIQUES WITHIN THE INVENTIVE AREA

Techniques for relieving problems with snoring arranged to affect chins, cheeks and mouth can either be intra-oral, i.e. aids arranged inside the mouth, or extra-oral, i.e. aids arranged outside the mouth.

There are several intra-oral patented or patent pending aids where most are within the category oral snoring splints, bite splints or dental splints often named Mandibular Advancement Devices, which can be described as "lower chin forward pulling aids", for example patents GB2264868, U.S. Pat. No. 6,109,265, CA2236503, CA2336604 and US2008115791. There are also intra-oral systems which stimulated the muscles and prevent relaxation of mouth and thong, for example patent WO02066111.

Known extra-oral system which facilitates breathing and/or prevents snoring have a wide spectra of solutions; different bandages supporting the chin, some actually first described for more than one hundred years ago (for example patents GB190709828 and GB191323245), and some more modern variants for example patents GB2264868, U.S. Pat. No. 6,109,265, CA2236503, CA2336604 and US2008115791. It is also described a stand like frame which supports the under jaw especially during narcosis (patent CN101422635), a special mask for the chin (patent JP2006175110), different sorts of supporting collars (for example patents GB191209390, U.S. Pat. No. 4,366,815, U.S. Pat. No. 5,289,829, U.S. Pat. No. 6,668,834), different sorts of pillows supporting chin and/or head (for example patents U.S. Pat. No. 4,118,813, U.S. Pat. No. 4,748,702, DE202004012390, US2007256694), more simple lip sealing adhesive tapes (patent JP11076286), to tapes completely covering the entire mouth (patent U.S. Pat. No. 4,817,636). It is also describes elastic bands which are placed under the chin and neck to give support from below (patent DE202004012829).

The previously described and known extra-oral aids are either not solving the problem, are uncomfortable, difficult to adjust individually or bulky, which creates discomfort and pressure on face, lips, chin, cheek, throat or jaw, and therefore these aids are not accepted for use by several snorers.

Solution to the Problem

An object of the present extra-oral invention in this application is to solve the described problems with prior art by using the features described in the following claims. The technical inventive step can be said to be the invention's essentially distinguishing and unique ability to individually and adjustably hook up the entire jaw angle, spread out the pulling force from the jaw angle, fixate the under jaw to the upper jaw and follow the curvature of the face up towards the upper jaw in the length direction where else the under jaw falls during sleep and this is done in a way which is simple, safe and careful for the user.

BRIEF DESCRIPTION OF DRAWINGS

The invention is now described, by way of example, with reference to the accompanying drawings, in which:

FIG. 1 shows both legs 1 of the splint which are creating a crotch 2 to distribute the pulling force and the arc-shaped part 3 which individually is bent behind the jaw angle in order to hook up the jaw angle and the shaft 4 of the splint for fixation to the upper jaw. The splint is adhered to the support in all its parts with a thin plaster, tape or similar 5. The shaft 4 of the splint can also be prolonged 8 over the bridge of the nose to give extra stability.

FIG. 2 shows the splints applied on both sides jaw angles 6 in order to support the entire lower jaw 7. The shaft 4 of the splint can be prolonged 8 over the bridge of the nose to give extra stability.

FIG. 3 shows the lower jaw without aid which normally falls downwards/backwards 9 during sleep.

FIG. 4 shows the lower jaw supported forwards-upwards 10 with a splint in the jaw angle 6 and fixated to the upper jaw.

FIG. 5 elucidates how the arc-shaped part 3 of the splint is hooked up behind the jaw angle 6 with the crotch 2 of the splint on each side in the angle and follows the curvature of the jaw angle.

DETAILED DESCRIPTION OF EMBODIMENTS

Figure 1:
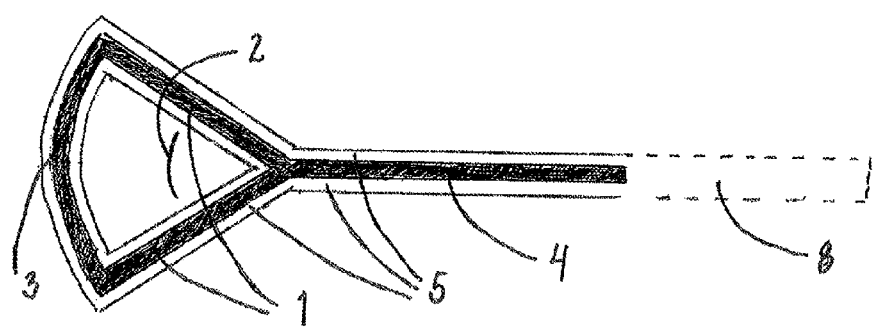
FIG. 1 Shows a principal sketch in a plan view from above of the splint
Figure 2:
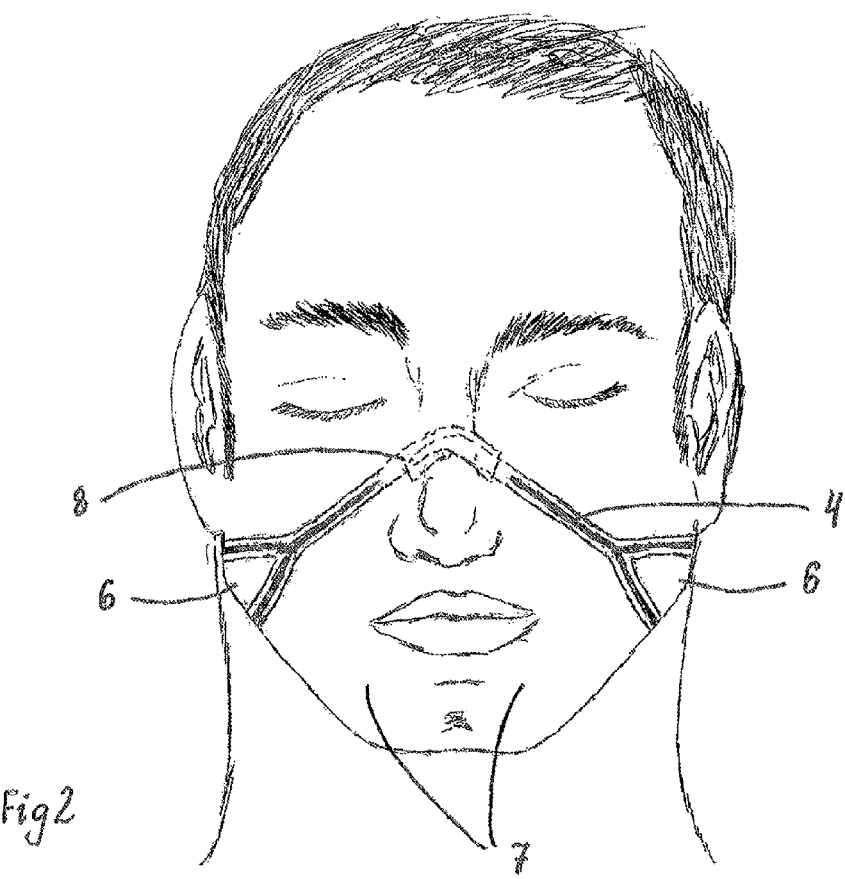
FIG. 2 Shows a sketch of splints placed on the face in a view from the front.
Figure 3:
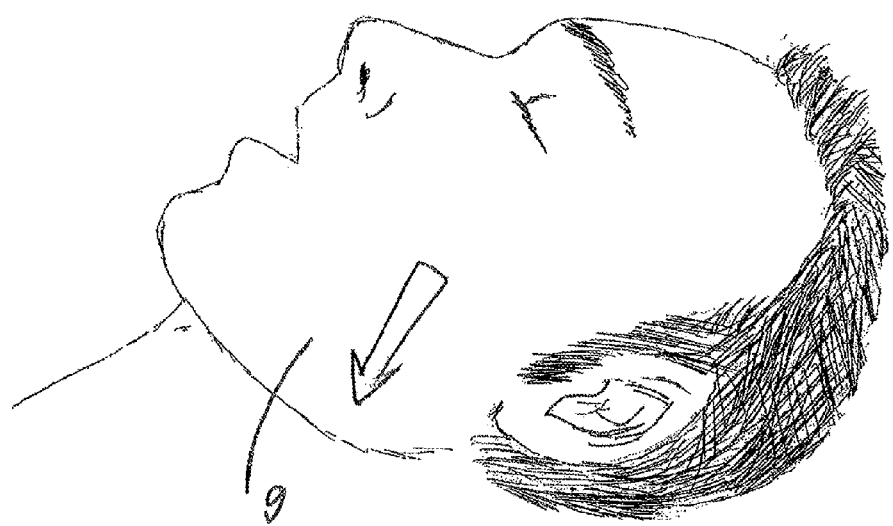
FIG. 3 Shows a sketch of the face in a side view without splint when the under jaw falls backwards-downwards during sleep.
Figure 4:
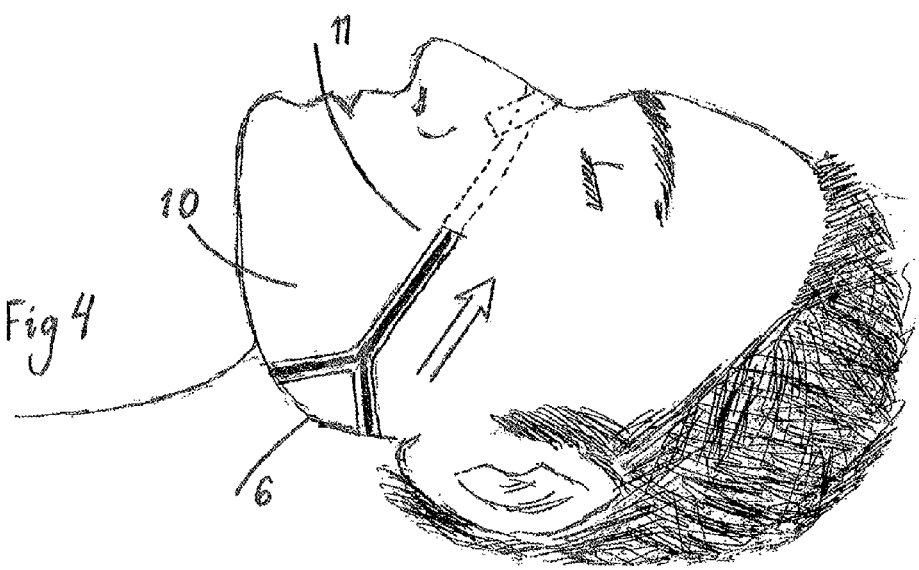
FIG. 4 Shows a sketch of the face in a side view with a splint in place on the face and supporting under jaw in a direction forwards-upwards during sleep.
Figure 5:
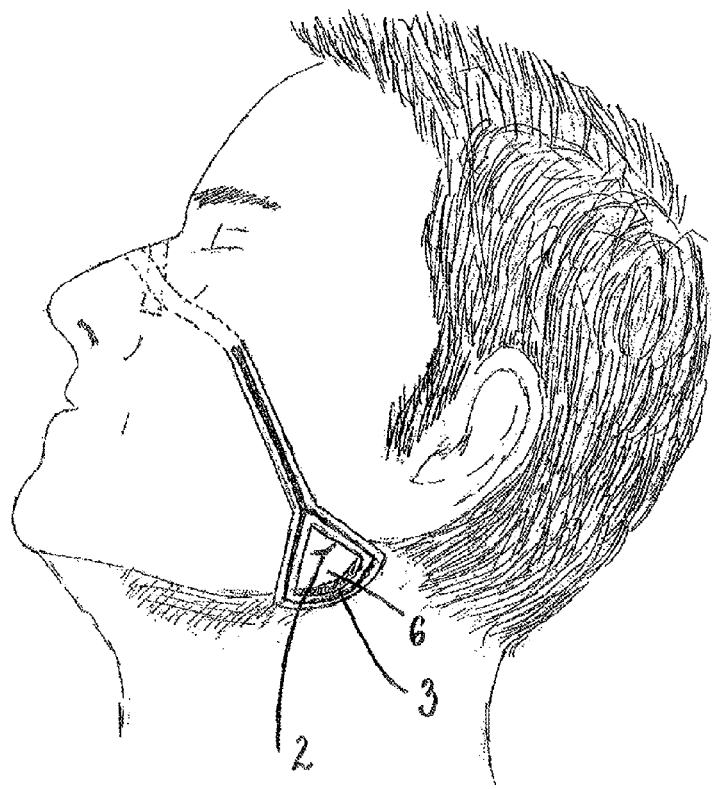
FIG. 5 Shows a sketch of the face as in FIG. 4, but leaning in a side view with splint in place on the face and supporting under jaw with an elucidation of the placement of the splint in the jaw angle.

The jaw angle is supported with a splint in one piece (FIG. 1) which has the shape of a slingshot; the crotch 2 of the Y-shape encloses each leg 1 the jaw angle 6 in order to distribute the pulling force in the splint and the legs of the crotch 2 are joined in their ends with an arc-shaped and bendable splint 3 which hook up behind the jaw angle 6. The arc shape and the bendability make it possible for the splint to bend around and behind the jaw angle, in order to safely hook up the jaw angle, independent of the user's individual shape and curvature of the jaw angle (FIG. 5). The shaft 4 of the splint continues from the under jaw 10 then up towards the cheek and upper jaw 11 in a direction upwards-forwards. The splint lays flat against the skin to not protrude and irritate the user and is bendable to be able to follow the user's individual curvature of the jaw angle and the individual contour of the face. The splint is non-elastic in all its length directions in order to facilitate the firmness and fixation. The shaft 4 of the splint can also continue 8 up over the bridge of the nose for extra firmness and stability. The splint is fixated to the support (the skin) in all its parts with an enclosing. On one side, towards the support, there is adhesive, such as skin friendly thin plaster, tape or similar 5. In order to obtain an optimized effect, splints are applied in each jaw angle to support the entire jaw angle on both sides (FIG. 2). When the jaw angle is fixated to the cheek and upper jaw, the under jaw and chin are prevented from falling backwards-downwards and obstructing the throat (as in FIG. 3) and in that way the airway in the throat is maintained and snoring is prevented (FIG. 4 and FIG. 5). The splint is cheap to produce, simple to apply before falling asleep, light and comfortable to wear both in an awaken condition and during sleep, adjustable to the jaw angle of the individual, adaptable after the contour of the face and creates no uncomfortable pressure on the tissues and structures of the face and throat.

The invention claimed is:

1. An aid against snoring and sleep apnea for support of a jaw angle of an individual, consisting of two splints, each splint being in one piece consisting of legs and a shaft connected to the legs at a crotch, the legs and shaft forming a Y-shape, each splint having an arc-shaped part which joins distal ends of the legs that join at proximal ends in the crotch,
  wherein the shaft is adapted to, extend to a cheek and an upper jaw of the individual,
  wherein each splint is adapted to hook up the jaw angle and support the jaw angle towards the upper jaw and the cheek in a direction forwards-upwards, and prevent the under jaw and chin from falling backwards-downwards,
  wherein each splint comprises a bendable material being non-elastic in its entire length direction,
  wherein each splint is bendable to follow the natural curvature of the jaw angle and contour of the face of the individual,
  wherein each splint comprises adhesive on an entire skin-side surface of the splint, and
  wherein the shaft of one splint is adapted to adhere to the shaft of the other splint.

2. The aid against snoring and sleep apnea of claim 1, wherein the bendable material is one of a plate of plastic, silicone, or metal.

3. The aid against snoring and sleep apnea of claim 1, wherein the adhesive is plaster.

4. The aid against snoring and sleep apnea of claim 1, wherein the adhesive is tape.

* * * * *